United States Patent
Haagsma-Van der Kouwe (10) Patent No.: US 10,285,730 B2
(45) Date of Patent: May 14, 2019

(54) DERMATOME, BLADE AND ASSEMBLY OF A DERMATOME AND A BLADE

(71) Applicant: Humeca Holding B.V., Enschede (NL)

(72) Inventor: Danielle Haagsma-Van der Kouwe, Borne (NL)

(73) Assignee: Humeca Holding B.V., Enschede (NL)

( * ) Notice: Subject to any disclaimer, the term of this patent is extended or adjusted under 35 U.S.C. 154(b) by 311 days.

(21) Appl. No.: 14/663,807

(22) Filed: Mar. 20, 2015

(65) Prior Publication Data

US 2015/0265301 A1    Sep. 24, 2015

(30) Foreign Application Priority Data

Mar. 21, 2014   (NL) ...................................... 2012487
Jan. 9, 2015    (NL) ...................................... 2014106

(51) Int. Cl.
*A61B 17/322*    (2006.01)
*A61B 17/3213*   (2006.01)

(52) U.S. Cl.
CPC ........ *A61B 17/322* (2013.01); *A61B 17/3213* (2013.01)

(58) Field of Classification Search
CPC ............ Y10T 29/49895; A61B 17/322; A61B 17/3213; A61B 2017/3225
See application file for complete search history.

(56) References Cited

U.S. PATENT DOCUMENTS

| | | | |
|---|---|---|---|
| 3,934,591 A | 1/1976 | Gleason | |
| 2009/0157095 A1 | 6/2009 | Barker | |
| 2010/0211173 A1 | 8/2010 | Bardos | |
| 2014/0074120 A1* | 3/2014 | Esarey | A61B 17/322 606/132 |

FOREIGN PATENT DOCUMENTS

| GB | 645289 | 10/1950 |
|---|---|---|
| GB | 1231083 | 5/1971 |

* cited by examiner

*Primary Examiner* — Jocelin C Tanner
(74) *Attorney, Agent, or Firm* — Marcus C. Dawes (57) ABSTRACT

The invention relates to a dermatome, comprising:
 a blade holder for holding a blade, said blade holder comprising at least one guiding element for guiding an oscillating movement of a said blade, and
 at least one spacer spaced apart from said blade holder for defining a cutting gap between a said blade held by said blade holder and said spacer,
 wherein
 said at least one guiding element and said at least one spacer define a curved path.
The invention further relates to a blade, suitable to be used in such a dermatome, as well as an assembly of such a dermatome and such a blade.

22 Claims, 7 Drawing Sheets

DERMATOME, BLADE AND ASSEMBLY OF A DERMATOME AND A BLADE

The invention relates to a dermatome, comprising:
- a blade holder for holding a blade, said blade holder comprising at least one guiding element for guiding an oscillating movement of a said blade, and
- at least one spacer that is spaced apart from said blade holder for defining a cutting gap between a said blade held by said blade holder and said at least one spacer, The invention further relates to a blade suitable for use in a dermatome. In particular the invention relates to dermatome blades. More in particular the invention relates to a dermatome blade apparently intended to be used in a dermatome according to the invention.

The invention also relates to an assembly of a dermatome and a blade.

Such a dermatome and blade are known perse. A dermatome is used for harvesting skin graft. The width of the skin graft is limited to the width of the skin that is in contact with the blade of the dermatome. For some surfaces, for example a thighbone, this width may be relatively large, while for other surfaces, such as the head where the skin is relatively tight to the skull, this width may be relatively small. In using the skin grafts a relatively large width may be preferred.

It is an object of the invention to be able to increase the width of a harvested skin graft by increasing the width of the contact area of the skin with the blade on at least some surfaces of a human being.

This object is achieved by a dermatome according to the preamble that is characterized in that said at least one guiding element and said at least one spacer define a curved path.

At least in a use position of the blade the blade is also curved. In particular a cutting edge of said blade is curved at least in said use position.

As a result of the curvature of the path defined by the at least one guiding element, the at least one spacer and at least in use said blade, the width of the contact area of the skin with the blade may be relatively large, such that the harvested skin graft has a relatively large width. For example for the head of a person, or other curved surfaces, in particular curved surfaces where the skin is relatively tight to the bone the contact area and thereby the width of the harvested skin may be increased with respect to a straight or uncurved blade and dermatome.

The curvature of the defined curved path may be any suitable curvature, for example, but not limited thereto, circular or elliptical. The curvature may optionally be variable over its length or may optionally be asymmetric. In case of a circular curvature the radius may be chosen as desired, for example in accordance with a curvature of a particular surface of a human being or an animal. Various dermatomes with various curvatures and/or radii may be provided, such that for a surface of a human being or animal a suitable dermatome with a suitable curvature may be selected. The radius may for example be chosen between 50-300 mm, in particular between 100-200 mm.

It is noted that said oscillating movement of the blade is in a direction parallel to a longitudinal direction of said blade, i.e. in a direction parallel to the cutting edge of the blade.

It is noted that the defined path of the at least one guiding element and the at least one spacer are curved in their longitudinal direction.

For example, three or more spaced apart guiding elements may be provided that are arranged such that together they define a curved path.

For example, three or more spaced apart spacers may be provided that are arranged such that together they define a curved path.

By increasing the number of spaced apart guiding elements or spacers the accuracy of the thereby defined curved path may be increased, as the spaced apart guiding elements or spacers will then more and more resemble a continuous curve.

In an embodiment of the invention said guiding element has a guiding surface and said spacer has a spacer surface, wherein said guiding surface and said spacer surface are curved.

Such a curved guiding surface and curved spacer surface define an accurate curved path.

In this embodiment the defined curved path of the at least one guiding element and the at least one spacer are the curved guiding surface and the curved spacer surface.

It is noted that said guiding element and/or said spacer surface may be either (substantially) continuous or discontinuous surfaces.

In an embodiment of the dermatome according to the invention, said dermatome comprises at least one locking means for locking a said blade to said blade holder, said at least one locking means defining a curved path.

The defined curved path of the at least one locking means is arranged opposite to said curved path defined by said at least one guiding element, thereby forming a curved space for containing said blade. If the blade is a flexible blade, it is bended in its curved shape by said curved paths of said at least one guiding element and said at least one locking element.

For example, three or more spaced apart locking elements may be provided that are arranged such that together they define a curved path.

By increasing the number of spaced apart locking elements the accuracy of the thereby defined curved path may be increased, as the spaced apart locking elements will then more and more resemble a continuous curve.

In an embodiment of the invention said locking means has a locking surface, wherein said locking surface is curved.

Such a curved locking surface defines an accurate curved path.

In this embodiment the defined curved path of the at least one locking means is the curved locking surface.

It is noted that said locking surface may be either a (substantially) continuous or discontinuous surface.

In another embodiment of the dermatome according to the invention the curvatures of the defined curved paths of the at least one guiding element, the at least one spacer and/or the at least one locking means are substantially equal.

An advantage of the curvatures of the defined curved paths of the at least one guiding element, the at least one spacer and/or the at least one locking means being substantially equal is that the thickness of the harvested skin graft may be substantially uniform over its width if a blade is chosen with a same curvature or if a flexible blade is bended to the same curvature between the guiding element and the spacer.

In particular, the curvatures of the guiding element, the spacer surface and/or the locking surface may be substantially equal.

Practically said dermatome comprises a driving means for driving a said blade in said oscillating movement with respect to said at least one guiding element or guiding surface.

Said driving means may be any known, suitable driving means. Said driving means may for example be, but is not limited thereto, electrically powered, for example by an optionally releasable connected battery or by a connection to the mains electricity net, or for example by compressed air.

In yet another embodiment of the dermatome according to the invention said driving means comprises a first connecting means for connecting to a respective second connecting means of said blade, which first connecting means is drivable in said oscillating movement with respect to said at least one guiding element or guiding surface.

For example, said first connecting means may comprise a protrusion or a recess that are arranged for being inserted in or to receive a corresponding recess or protrusion of the second connecting means.

In yet another embodiment of the dermatome according to the invention said at least one guiding element or guiding surface comprises guiding means for guiding the oscillating movement of a said blade with respect to said at least one guiding element or guiding surface.

Said guiding means may for example comprise a stop (surface) suitable for receiving said blade in an abutting position.

In use said blade abuts to said stop (surface) and is thereby held in a correct, aligned position with respect to the at least one spacer or spacer surface. Said stop (surface) may for example be an upstanding element or edge connecting to a longitudinal end zone of said at least one guiding element or guiding surface. Said edge may be continuous over its end or may be interrupted.

Alternatively or additionally said guiding means may comprise guiding cams or guiding recesses that are arranged for being inserted in or to receive corresponding guiding recesses or guiding cams of a said blade. Such guiding cams and recesses may also help positioning said blade with respect to the at least one guiding element or guiding surface at inserting said blade.

In yet another embodiment of the dermatome according to the invention said at least one spacer is movably mounted with respect to said guiding element, such that the width of the cutting gap is adjustable.

Such a movable spacer offers the advantage of being able to adjust the width of the cutting gap and thereby the thickness of the skin graft.

In an embodiment of the blade according to the invention, said blade is flexible such that it is bendable in a curved shape between said at least one guiding element or guiding surface and said at least one locking means or locking surface.

By bending the blade in the curved shape between the at least one guiding element or guiding surface and at least one locking means or locking surface, the blade may easily adapt to any defined curvature thereof. This way, only one type of blade may be provided that can be used for various defined curvatures of the at least one guiding element or guiding surface and at least one locking means or locking surface. The blade may for example be sufficiently thin and/or made out of a suitable material to provide said flexibility. The blade is at least flexible in its longitudinal direction, i.e. in a direction parallel to a cutting edge thereof, such that the cutting edge of the blade can be bend in a curved shape.

Alternatively, said blade may have a curved shape adapted to the curved path defined by the at least one guiding element. Such a blade is permanently fixed in its curved shape. Although such a blade may be used for one curvature only, such that optionally different types of blades having different curvatures need to be provided, such a curved blade may be easier to insert in said blade holder.

Said blade, either curved or flexible, may comprise second connecting means for connecting to the first connecting means of the driving means.

Said blade, either curved or flexible, may comprise recesses or guiding cams that are arranged for being inserted in or to receive corresponding guiding cams or recesses of the guiding means. Such recesses or guiding cams may help position the blade in a correct position and/or may guide the oscillating movement of the blade.

The invention further relates to a dermatome according to the invention comprising any one or any combination of the above described features and a blade comprising any one or any combination of the above described features, wherein said blade is held by the blade holder of the dermatome.

The invention will be further elucidated with reference to figures shown in a drawing, in which:

FIGS. 1-7 show a dermatome 1 according to an embodiment of the invention. Similar elements are denoted by similar reference numerals.

Figure 1:
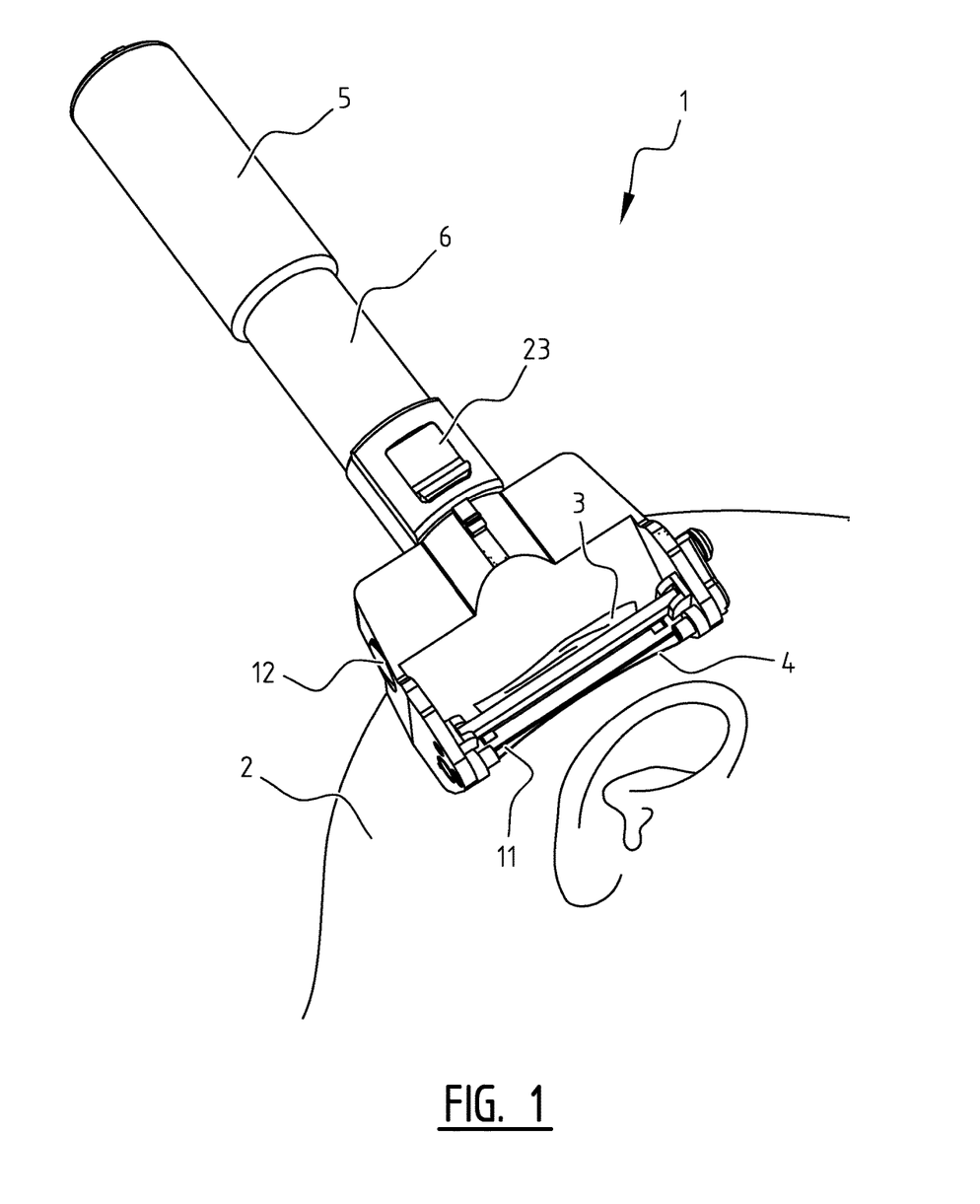
FIG. 1 is a perspective view of a dermatome according to an embodiment of the invention in use.
Figure 2:
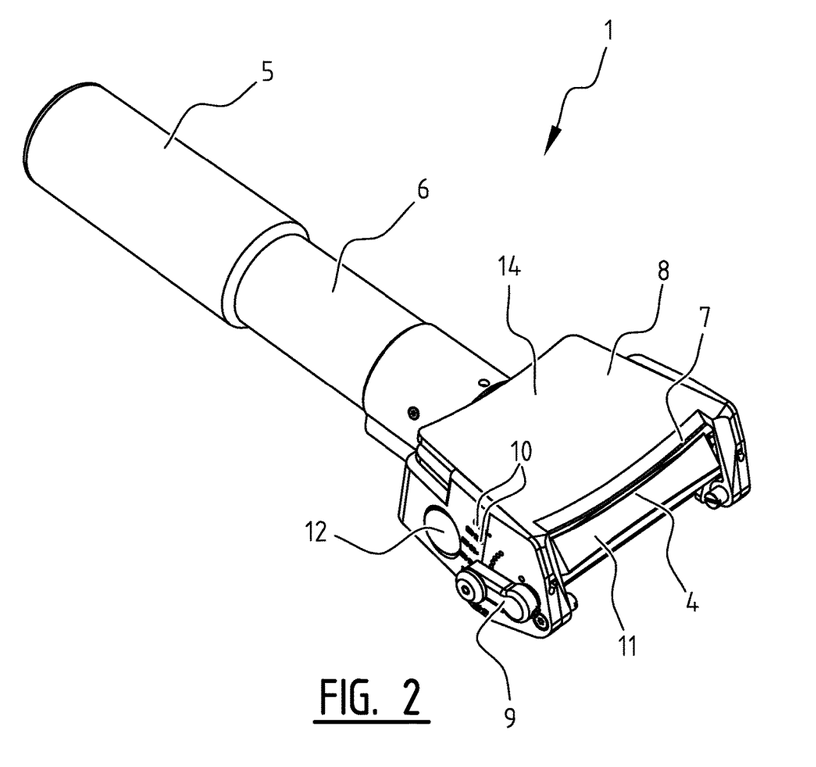
FIG. 2 is a perspective view of the other side of the dermatome of FIG. 1.

In FIG. 1, the dermatome 1 is shown in use for harvesting skin graft 3 from a head 2 of a human being. As is clearly shown in this FIG. 1, a spacer surface 4 of a spacer element 11 is curved, such that it corresponds to the curved shape of the head 2, in this example. As a result of this curvature the contact area with the head 2 is relatively large as compared to a straight or uncurved spacer element and thereby the width of the skin graft 3 is also relatively large. The dermatome 1 has a grip 5 containing a battery, which grip 5 is connected to a shaft 6 of the dermatome 1. A button 23 is shown for activating the dermatome 1. To the sides of the dermatome 1 two buttons 12 are provided, which may be pressed simultaneously for opening a locking element 14 of the dermatome 1. FIG. 2 shows the other side of the dermatome 1. The dermatome has a contact surface 8 that may be put in contact with the skin of a human being or animal. This contact surface 8 is curved to correspond to a curved surface of the human being. The contact surface 8 is part of the locking element 14 for locking the blade 7 to the blade holder, see also FIG. 4. A frontal longitudinal edge of the blade 7 extends slightly beyond the contact surface 8, such that it may contact the skin for cutting the skin. The spacer surface 4 is located at a predetermined distance from the blade 7, thereby defining a cutting gap 13 (see FIG. 3) between the spacer surface 4 and the blade 7, which defines the thickness of the skin to be harvested. To the side of the dermatome 1 a handle 9 is provided, which is connected to the spacer element 11 for moving the spacer element 11 with respect to a guiding surface 15 (see FIG. 4) of the dermatome for adjusting the width of the cutting gap. Denoted by number 10 are fixed positions for the handle 9, such that the desired position of the spacer element 11 may easily be selected. Instead of fixed positions the spacer element 11 may be adjustable in a continuous way.

Figure 3:
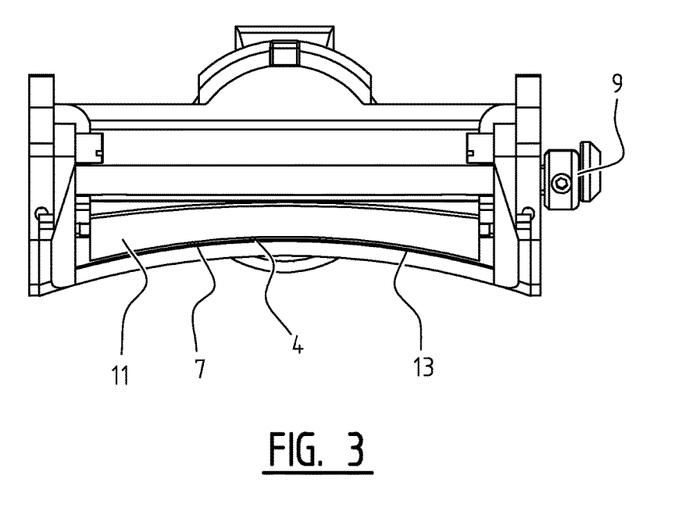
FIG. 3 is a front view of the dermatome of FIG. 1.

FIG. 3 is a frontal view of the dermatome 1. From this figure it is clear that the curvatures of the blade 7 and the spacer surface 4 are substantially equal. In particular the inner radius of the blade 7 is equal to the outer radius of the spacer surface 4. The radius is 160 mm in this example. The small gap 13 located between the blade 7 and the spacer surface 4 has therefore a substantially uniform thickness over its length, such that the thickness of the harvested skin graft is substantially uniform. It is noted that in particular for one position of the adjustable spacer element 11 the small gap 13 has a uniform thickness over its length, for example for a position of the spacer element 11 that is most frequently used. In the other positions of the adjustable spacer element the small gap 13 may have a thickness that is almost or substantially equal over its length.

Figure 4:
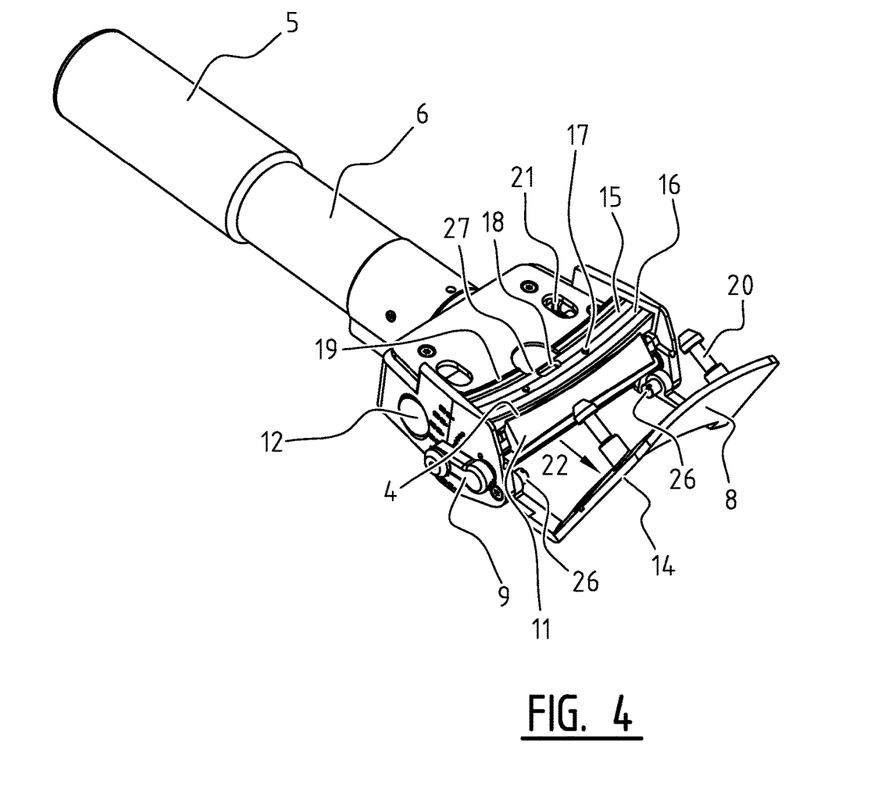
FIG. 4 is the perspective view of FIG. 2 in a position for inserting a blade.

FIG. 4 shows the dermatome 1 in the position of FIG. 2, wherein the locking element 14 comprising said contact surface 8 is opened to an open position for inserting the blade 7. This shows that the dermatome 1 has a guiding surface 15 with a curvature that corresponds to the curvatures of the blade 7 and spacer surface 4, or will bend the blade 7 in the desired curvature. The locking element 14 has a locking surface 22 with a curvature corresponding to the curvatures of the guiding surface 15 and the spacer surface 4. The locking surface 22 is located opposite to the contact surface 8. The blade 7 may be arranged on the guiding surface 15 for inserting the blade 7 to the blade holder. The guiding surface 15 has a longitudinal groove 16 for decreasing the contact area between the guiding surface 15 and the blade 7 and thereby the friction therebetween. The guiding surface 15 further has two guiding cams 17 and an upstanding edge 19. A protrusion 18 of a driving means is also provided, which protrusion 18 is drivable in an oscillating movement with respect to the guiding surface 15 in the longitudinal direction thereof. Said protrusion 18 is oscillating in a elongated slot or recess 27 extending in the longitudinal direction of the guiding surface 15. The movement of the protrusion 18 is electrically driven by a motor electrically powered by said battery. After inserting a blade 7 the locking element 8 may be closed for locking the blade 7 to the blade holder by inserting locking pins 20 of the locking element 14 in respective locking recesses 21 of an opposing surface of the dermatome 1. As described above, two buttons 12 may be pressed simultaneously for releasing the locking pins 20 from the locking recesses 21 and for opening the locking element 14. The locking element 14 is pivotable between its open position shown in FIG. 4 and its closed position shown in FIG. 2 via hinges 26.

Figure 5:
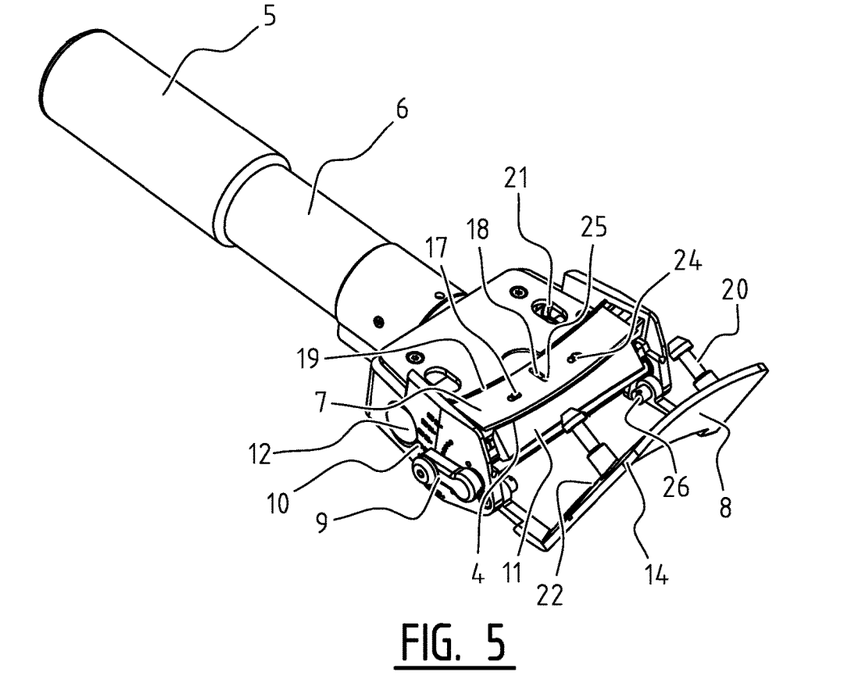
FIG. 5 is the perspective view of FIG. 4 with an inserted blade.

FIG. 5 shows the blade 7 in inserted position. This shows that the blade 7 has two elongated slots or recesses 24 extending in the longitudinal direction of the blade 7 and an elongated slot or recess 25 extending in a transverse direction of the blade 7. The recesses 24 are arranged for receiving the guiding cams 17 of the guiding surface 15 and the recess 25 is arranged for receiving the protrusion 18 of the driving means. The recesses 24 have a length such that the guiding cams 17 do not reach the end zones thereof during the oscillating movement of the blade 7. The guiding cams 17 therefore, in at least this embodiment, do not limit the maximum oscillating movement of the blade 7. The guiding cams 17 provide an easy alignment of the blade 7 to the guiding surface 15, and may therefore also be seen as alignment or positioning cams. A rear end zone of the blade 7 abuts against the upstanding edge 19, which edge 19 holds the blade 7 in a correct position during use of the dermatome 1. The recess 25 extends over a certain length in the transverse direction for allowing some movement of the protrusion 18 in the transverse direction and/or some movement of the blade 7, such that the blade 7 may easily be inserted and may abut said edge 19.

Figure 6:
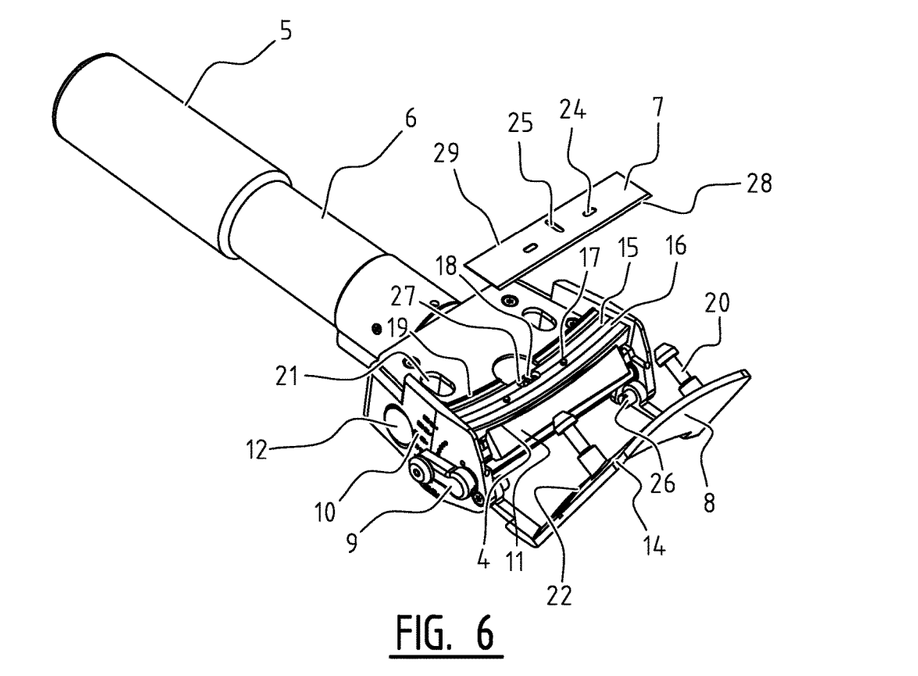
FIGS. 6 and 7 show two types of blades suitable to be used with the dermatome of FIG. 1.

FIG. 6 shows a first type of blade 7. The blade 7 is a straight, flexible blade, such that it is bendable in a curved position. The blade is at least flexible in the longitudinal direction thereof. After insertion of the blade to the guiding surface 15 and closing the locking element 14, the blade 7 is bended to its curved position therebetween. The curvature of the blade 7 is thereby determined by the curvatures of the guiding surface 15 and locking surface 22. For providing the blade 7 flexibility the blade 7 may for example be made of a flexible material an/or may be relatively thin. As is shown, the blade 7 comprises two recesses 24 and one recess 25. A front longitudinal end zone 28 is a cutting zone of the blade 7 and the rear longitudinal end 29 abuts said edge 19.

Figure 7:
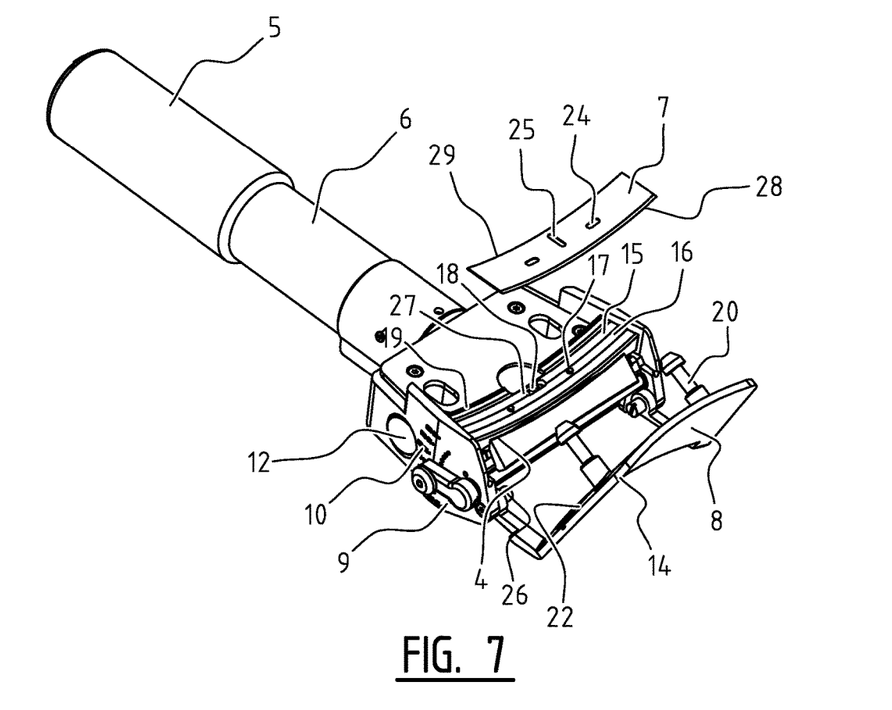

FIG. 7 shows a blade 7 that is permanently curved. Said blade may have any desired curvature. Various blades 7 with various curvatures may optionally be provided, such that for harvesting skin graft from a particular surface a blade 7 with a suitable curvature may be chosen, also in accordance with a curvature of at least the guiding surface 15 and spacer surface 4 of the dermatome 1. As is shown, the blade 7 comprises two recesses 24 and one recess 25. A front longitudinal end zone 28 is a cutting zone of the blade 7 and the rear longitudinal end 29 abuts said edge 19.

It is noted that the invention is not limited to the shown embodiments but also extends to variants within the scope of the appended claims.

For example, it is clear for the skilled person that the blade may have a protrusion and guiding cams, and said receiving surface may have a drivable recess and recesses for receiving the guiding cams.

Also, it is clear that the various curvatures of the guiding surface, the spacer surface, the locking surface and the blade may be any desired curvature and are not limited to the circular curvatures that are shown in the figures.

It is also clear for the skilled person that instead of a guiding surface and/or spacer surface and/or a locking surface a plurality of guiding elements and/or spacers and/or locking elements may be provided that define a curved path.

The grip may alternatively comprise a connecting means for connecting to the mains electricity grid instead of accommodating a battery.

For inserting the blade to the blade holder it may optionally be positioned on the locking surface.

The invention claimed is:

1. A dermatome, comprising:
   blade;
   a blade holder for holding the blade, the blade holder comprising at least one guiding surface for facilitating an oscillating movement of the blade in a longitudinal direction of the blade relative to the at least one guiding surface;
   at least one spacer that is spaced apart from the blade holder for defining a cutting gap between the blade held by the blade holder and the at least one spacer; and
   at least one lock to lock the blade to the blade holder, wherein the at least one guiding surface, the at least one spacer and the at least one lock define a first, second, and third radius of curvature respectively, wherein the blade is flexible such that it bends into a non-flat shape between the first radius of curvature of the at least one guiding surface and the third radius of curvature of the at least one lock.

2. The dermatome according to claim 1, wherein the first or second radius of curvature is substantially equal with the third radius of curvature.

3. The dermatome according to claim 1, comprising a driver to drive the blade in an oscillating movement in a longitudinal direction of the blade relative to the at least one guiding surface.

4. The dermatome according to claim 3, wherein the driver comprises a first connector to connect to a respective second connector of the blade, which first connector is drivable in an oscillating movement in a longitudinal direction of the blade relative to the at least one guiding surface.

5. The dermatome according to claim 4, wherein the first connector comprises a protrusion or a recess that is arranged for being inserted in or to receive a corresponding recess or protrusion of the second connector.

6. The dermatome according to claim 1, wherein the at least one guiding surface comprises a guide to guide an oscillating movement of the blade in a longitudinal direction of the blade relative to the at least one guiding surface.

7. The dermatome according to claim 6, wherein the guide comprises a stop surface suitable for receiving the blade in an abutting position.

8. The dermatome according to claim 6, wherein the guide comprises guiding cams or guiding recesses that are arranged for being inserted in or to receive corresponding guiding recesses or guiding cams of the blade.

9. The dermatome according to claim 1, wherein the at least one spacer is movably mounted with respect to the at least one guiding surface, such that a width of the cutting gap is adjustable.

10. The dermatome according to claim 1, wherein:
the at least one spacer has a spacer surface;
the at least one lock has a locking surface;
the guiding surface and the spacer surface of the at least one spacer are bent into the first radius of curvature and the radius of curvature, respectively; and
the locking surface is bent into the third radius of curvature.

11. The blade according to claim 1, further comprising a driver to drive the blade in an oscillating movement in a longitudinal direction of the blade relative to the at least one guiding surface, wherein the driver comprises a first connector and a second connector to connect to the first connector.

12. The blade according to claim 1, wherein the at least one guiding surface comprises a guide to guide an oscillating movement of the blade in a longitudinal direction of the blade relative to the at least one guiding surface, and wherein the blade comprising recesses or guiding cams that are arranged to receive or for being inserted in corresponding guiding cams or recesses of the guide.

13. A dermatome, comprising:
a blade;
a blade holder for holding the blade, the blade holder comprising at least one guiding surface for facilitating an oscillating movement of the blade in a longitudinal direction of the blade relative to the at least one guiding surface;
at least one spacer that is spaced apart from the blade holder for defining a cutting gap between the blade held by the blade holder and the at least one spacer;
wherein the at least one guiding surface and the at least one spacer define a first and second radius of curvature respectively, wherein the blade has a curved shape adapted to the first radius of curvature defined by the at least one guiding surface.

14. The dermatome according to claim 13, comprising a driver to drive the blade in an oscillating movement in a longitudinal direction of the blade relative to the at least one guiding surface.

15. The dermatome according to claim 14, wherein the driver comprises a first connector to connect to a respective second connector of the blade, which first connector is drivable in an oscillating movement in a longitudinal direction of the blade relative to the at least one guiding surface.

16. The dermatome according to claim 15, wherein the first connector comprises a protrusion or a recess that is arranged for being inserted in or to receive a corresponding recess or protrusion of the second connector.

17. The dermatome according to claim 13, wherein the at least one guiding surface comprises a guide to guide an oscillating movement of the blade in a longitudinal direction of the blade relative to the at least one guiding surface.

18. The dermatome according to claim 17, wherein the guide comprises a stop surface suitable for receiving the blade in an abutting position.

19. The dermatome according to claim 17, wherein the guide comprises guiding cams or guiding recesses that are arranged for being inserted in or to receive corresponding guiding recesses or guiding cams of the blade.

20. The dermatome according to claim 13, wherein the at least one spacer is movably mounted with respect to the at least one guiding surface, such that a width of the cutting gap is adjustable.

21. The dermatome according to claim 13, comprising at least one lock to lock the blade to the blade holder, the at least one lock defining a second radius of curvature.

22. The dermatome according to claim 21 wherein the defined first and second radius of curvatures are substantially equal.

* * * * *